United States Patent [19]

Lau et al.

[11] Patent Number: 5,288,908
[45] Date of Patent: Feb. 22, 1994

[54] PROCESS FOR THE PREPARATION OF FLUORINE CONTAINING MONOMERS

[75] Inventors: Jürgen Lau; Günter Siegemund, both of Hofheim am Taunus; Freimund Röhrscheid, Kelkheim, all of Fed. Rep. of Germany

[73] Assignee: Hoechst Aktiengesellschaft, Frankfurt am Main, Fed. Rep. of Germany

[21] Appl. No.: 93,932

[22] Filed: Jul. 19, 1993

Related U.S. Application Data

[60] Division of Ser. No. 998,883, Dec. 28, 1992, which is a continuation of Ser. No. 413,833, Sep. 28, 1989, abandoned.

[51] Int. Cl.$^5$ .................. C07C 209/36; C07C 209/42
[52] U.S. Cl. .......................... 564/335; 534/578; 534/843; 562/416; 562/417; 562/435; 562/491; 564/139; 564/166; 564/315; 568/812; 570/129; 570/142
[58] Field of Search ............... 564/335, 139, 166, 315; 534/573, 578, 843; 562/417, 416, 435, 491; 568/812; 570/129, 142

[56] References Cited

U.S. PATENT DOCUMENTS

| | | | |
|---|---|---|---|
| 3,310,573 | 3/1967 | Coe | 564/220 |
| 3,356,648 | 12/1967 | Rogers | 528/353 |
| 4,370,501 | 1/1983 | Lau | 564/330 |
| 4,645,824 | 12/1987 | Landis et al. | 548/541 |
| 4,711,964 | 12/1987 | Tan et al. | 548/461 |
| 4,758,380 | 7/1988 | Alston et al. | 549/241 |
| 4,952,669 | 8/1990 | Vora | 528/353 |

FOREIGN PATENT DOCUMENTS 3526010 1/1986 Fed. Rep. of Germany .

OTHER PUBLICATIONS

Farah et al., *J. Org. Chem.*, vol. 30, pp. 998-1001 (1965).

*Primary Examiner*—Glennon H. Hollrah
*Assistant Examiner*—Scott C. Rand
*Attorney, Agent, or Firm*—Connolly & Hutz

[57] ABSTRACT

Compounds of the formula

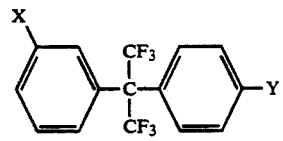

(I)

in which X represents hydrogen, $-NO_2$ or $-NH_2$ and Y represents $-CH_3$, $-COOH$, $-CONH_2$, $-NH_2$ or $-N=N-Z$, in which the group $-Z$ is

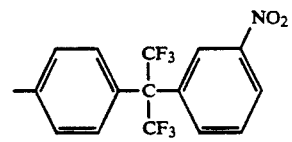

with the proviso that if Y represents the group $-N=N-Z$, X is only $-NO_2$, and if Y represents the group $-CH_3$, X is only hydrogen, are described. A compound of the formula

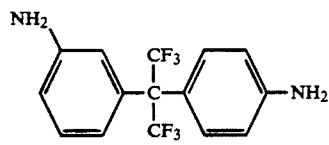

(II)

the preparation of which in a multi-stage process, in which the compounds of the general formula (I) are also obtained, is described, is preferred.

The resulting 3,4'-diamino compound is suitable for the preparation of polycondensates and shaped articles, films and fibers of high heat resistance.

15 Claims, No Drawings

PROCESS FOR THE PREPARATION OF FLUORINE CONTAINING MONOMERS

This application is a divisional application of U.S. patent application Ser. No. 07/998,883, filed Dec. 28, 1992, now pending, which is a continuation of U.S. patent application Ser. No. 07/413,833, filed Sep. 28, 1989, now abandoned.

DESCRIPTION

The invention relates to fluorine-containing monomers and their preparation, in particular 2-(3-aminophenyl)-2-(4-aminophenyl)hexafluoropropane, a novel fluorine-containing monomer for polycondensates of high heat resistance, such as polyamides and polyamides.

It is known that transparent polymers of high heat stability can be prepared from 2,2-bis(3-aminophenyl)hexafluoropropane and 2,2-bis(4-aminophenyl)hexafluoropropane (U.S. Pat. No. 3,356,648, DE-OS 3,526,010 and U.S. Pat. No. 4,645,824). On the basis of the above properties, is these polymers are used as high quality materials, for example in the aircraft and electronics industries.

The object was based on preparing a partly fluorinated diamine with which polycondensates which combine the properties of the polycondensates based on the above-mentioned structurally isomeric diamino compounds can be obtained.

The invention relates to novel compounds of the formula

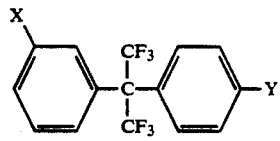

(I)

where
X = hydrogen, NO₂ or NH₂ and
Y = CH₃, COOH, CONH₂, NH₂ or —N=N—Z, in which Z is the group

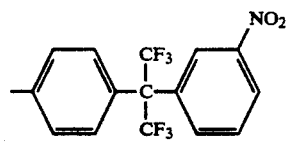

with the proviso that if Y represents the group —N=N—Z, X is only NO₂, and if Y represents the group —CH₃, X is only hydrogen, preferably 2-(3-aminophenyl)-2-(4-aminophenyl)hexafluoropropane (II), and to processes for their preparation and their use.

The compound (II) is obtained by six reaction steps starting from 2-(4-methylphenyl)hexafluoropropan-2-ol or 2-phenyl-hexafluoropropan-2-ol. The intermediate products formed here are likewise novel.

The methyl compound (III) can be prepared by two processes, and in particular a) by condensation of one mol of 2-(4-methylphenyl)hexafluoropropan-2-ol with one mol of benzene or b) by condensation of one mol of 2-phenylhexafluoropropan-2-ol with one mol of toluene in the presence of hydrogen fluoride. The starting compounds are known and are described in J.O.C., 998-1001, 30 (1965). The reaction temperatures in processes a) and b) are between 80° and 180° C., preferably between 100° and 170° C. The reaction times are 24 to 90, preferably 65 to 90 hours. The molar ratio of the reaction partners employed is in both cases in general 1:5, preferably 1:1.5 to 2.5, the compounds benzene and toluene always being the components in excess. The amount of hydrogen fluoride needed for the reaction to prepare the compound (III) is based on the corresponding starting compound and is in both processes in general in the molar ratio of 1:7 to 25, preferably 1:9 to 20. For working up the reaction mixture, the hydrogen fluoride is in general gassed out of the reactor at about 80° C. when the reaction has ended. The resulting crude mixture is washed with water, dried and subjected to fractional distillation.

The methyl compound (III) can be oxidized by the customary stoichiometric methods, using, for example, potassium permanganate, chromic acid/glacial acetic acid, dichromate/sulfuric acid or, preferably, catalytically using molecular oxygen in the presence of a catalyst combination of the ions of cobalt, manganese and bromine, to give the carboxylic acid (IV); the reaction being carried out in an acid medium which consists to the extent of at least 40% of acetic acid or propionic acid or mixtures thereof. Acetic acid is to be preferred because of its higher resistance towards oxidative degradation. The ratio of acid medium to starting substance employed can be up to a ratio of 40:60% by weight, based on the total reaction mass.

Bromide ions are absolutely essential for the complete course of the oxidation. The cobalt and manganese ions are in general employed in a ratio of 3:1 to 1:3, preferably 1:1. The sum of the concentrations of the two elements is in general 0.01 to 0.2, preferably 0.02 to 0.12 and in particular 0.04 to 0.08 g atoms/kg of total mass. The ratio of the sum of cobalt and manganese to bromine is in general 1:0.01-2, preferably 1:0.025-1 and in particular 1:0.05-0.2. It is also possible for cerium ions also to be employed in addition to the two metal ions of the catalyst. These catalyze the oxidation of incompletely oxidized intermediate stages. Their presence increases the purity and yield of the partly fluorinated monocarboxylic acid. The cerium ions are added to the catalyst in a ratio of the sum of cobalt and manganese ions to cerium ions of 1:0.02-2, preferably 1:0.05-1 and in particular 1:0.2-0.6. The metal ions are preferably employed in the form of their acetates.

Bromine can be employed in the form of bromides, for example the bromides of alkali metals, including ammonium bromide, and those of the metals cobalt, manganese and cerium, or as a solution of hydrogen bromide in water or glacial acetic acid. In addition, bromine-containing organic compounds which dissociate during the oxidation and liberate bromine ions, for example tetrabromomethane, can also be used.

The oxidation is in general carried out at temperatures from 120° to 220°, preferably 140° to 190° and in particular 155° to 180° C. The pressure in the reactor is in general between 5 and 40, preferably between 10 and 30 and in particular between 14 and 20 bar.

It is advantageous for the procedure for the air required for the oxidation to be introduced into the liquid phase close to the bottom of the reactor and to be finely dispersed in the liquid phase by vigorous stirring or by special jets.

In the third reaction step, the 2-(4-carboxyphenyl)-2-(3-nitrophenyl)hexafluoropropane (V) is prepared from the carboxylic acid (IV) by a nitration reaction. Generally customary nitrating acid mixtures, for example nitric acid/sulfuric acid, nitric acid/glacial acetic acid, nitric acid/acetic anhydride or nitric acid/water mixtures, can be used for the nitration. 98% strength nitric acid is particularly suitable for the nitration, the carboxylic acid being dissolved in an organic solvent, for example tetrahydrofuran, dioxane, glacial acetic acid, ethanol, halogenated aliphatic hydrocarbons having up to 3 carbon atoms, preferably methylene chloride, and concentrated sulfuric acid. The concentrated nitric acid is then added in portions each of small amounts at a temperature from minus 20° to plus 50° C., preferably at minus 5° to plus 5° C. The compound (V) is then converted into the 2-(4-carboxamidophenyl)-2-(3-nitrophenyl)hexafluoropropane (VI). The generally customary methods for the preparation of carboxamides from carboxylic acids can be used to prepare the carboxamide (VI). Direct reaction of the carboxylic acid (V) with amidosulfonic acid in a reaction mixture of sulfuric acid/oleum at a temperature of 50° to 180° C., preferably 90° to 100° C., is particularly suitable.

In the fifth reaction step, the carboxamido compound (VI) is reacted with aqueous hypohalide solutions under the conditions of the "Hofmann" rearrangement in the presence of bases at reaction temperatures of 5° to 70° C., preferably about 40° C. Surprisingly, only minor amounts of the expected 2-(4-aminophenyl)-2-(3-nitrophenyl)hexafluoropropane (VIIa) are obtained here. The predominant proportion of the reaction product is 4,4'-bis[2-(3-nitrophenyl)hexafluoropropane]azobenzene (VII). 5 to 30% strength aqueous solutions of alkali metal hypochlorides and hypobromides, preferably an approximately 13% strength sodium hypochloride solution, are employed as the hypohalide solutions in the presence of 5-50% by weight of a base, for example an alkali metal hydroxide or ammonium bases. Phase transfer catalysts, for example tetraalkylammonium salts, benzyltrialkylammonium salts, benzyltrialkylphosphonium salts, benzyltriphenylphosphonium salts, tetraalkylphosphonium salts having in each case 1-6 carbon atoms in the alkyl radical, crown ethers or polyethylene glycols, can be added in amounts of 0.1 to 20 mol % to accelerate the reaction.

In addition to the azo compound (VII), which the crude product contains to the extent of about 70%, a small amount that is to say up to 15% of 2-(4-aminophenyl)-2-(3-nitrophenyl)hexafluoropropane (VIIa) is formed as a further product in the fifth reaction step. The pure azo compound (VII) can be obtained by recrystallization of the crude product from an organic solvent, for example ethanol, acetonitrile, ethyl acetate, methylene chloride, chloroform or carbon tetrachloride, preferably ethanol. However, it is not necessary to isolate the azo compound (VII) from the crude product in order to prepare the 2-(3-aminophenyl)-2-(4-aminophenyl)hexafluoropropane (II), since the compound (II) is obtained both from the compound (VII) and from (VIIa). The reduction of the nitro and azo group in the compounds (V), (VI), (VII) and (VIIa) can be carried out, for example, by the customary catalytic methods using hydrogenation catalysts of a transition metal, in particular of sub-group VIII of the Periodic Table, or by stoichiometric methods (for example with tin(II) chloride/glacial acetic acid). Platinum metals, copper, iron, cobalt, nickel, metal oxides or mixed metal catalysts, for example, can be employed for the catalytic reductions, preferably without or with the use of increased pressure in customary diluents, such as lower aliphatic alcohols, aromatic hydrocarbons (for example toluene or xylene), aliphatic monocarboxylic acid esters or similar organic solvents, at temperatures of, for example, 10°-130° C. For purification of the compound (II), this can be converted at, for example, 10°-100° C. with acids into one of its water-soluble salts (for example halide or hydrogen sulfate) which is inert towards amino groups under the conditions used.

The 3,4'-diamino compound obtained is suitable for the preparation of polycondensates of high heat resistance. Polyamides are obtained by reaction with tetracarboxylic acids or derivatives thereof. On the other hand, reaction with dicarboxylic acid chlorides gives polyamides. The polyamides have, for example, low dielectric constants.

Novel monomers and oligomers can moreover be obtained, for example by reaction by dianhydrides. The resulting imide monomers and oligomers can be hardened by addition reactions. The diamine according to the invention is moreover suitable for the preparation of polymeric precursors, epoxide hardeners, matrix resins, laminates, films, fibers, adhesives, coatings, photoresists and shaped articles.

EXAMPLES 1) 2-(4-Methylphenyl)-2-phenylhexafluoropropane (III)

a) 1,290 g of 2-(4-methylphenyl)hexafluoropropan-2-ol and 780 g of benzene were initially introduced into a 5 l steel autoclave and 1,500 g of anhydrous hydrogen fluoride were pumped into the closed autoclave. The reaction mixture was heated at 170°-175° C. for 64 hours, while stirring. When the reaction had ended, the hydrogen fluoride was gassed off at 80° C. and the liquid product was then washed twice with water, dried over calcium chloride and subjected to fractional distillation. Boiling point 135°-136° C./1.4 mbar. Amount weighed: 1,424 g (89.5% of theory).

$C_{16}H_{12}F_6$ calculated: C, 60.38%; H, 3.77%; F, 35.85%; molecular weight: 318 found: C, 60.50%; H, 3.70%; F, 35.80%.

b) 244 g of 2-phenylhexafluoropropan-2-ol, 368 g of toluene and 180 g of anhydrous hydrogen fluoride were combined in a 1 l V4A steel autoclave with a stirrer. The reaction mixture was then stirred at 175° C. for 65 hours. After cooling to 80° C., the hydrogen fluoride was gassed off. The crude product was washed twice with water, dried over calcium chloride and subjected to fractional distillation. Boiling point 82° C./0.05 mbar. 67 g $\triangleq$ 21% of theory.

2) 2-(4-Carboxyphenyl)-2-phenylhexafluoropropane (IV)

298 g of 2-(4-methylphenyl)-2-phenylhexafluoropropane, 2.49 g of cobalt(II) acetate tetrahydrate, 2.45 g of manganese(IV) acetate tetrahydrate and 0.41 g of hydrogen bromide (corresponding to 4.1 g of a 10% strength HBr solution in glacial acetic acid) were initially introduced into a 1 l glass autoclave. The mixture was heated to about 180° C. under an oxygen pressure of 6.5 bar and under an exothermic reaction and was left at 170°-180° C. for 1 hour. The reaction solution was cooled to about 100° C. and 200 g of acetic acid were then distilled off. 275 g of water were slowly added to the solution remaining in the flask (about 600 g) at the boiling point. The carboxylic acid which had crystallized out was filtered off with suction, washed twice with 75 ml of 50% strength aqueous acetic acid each time and five times with 85 ml of water each time and dried at 60° C./60 mbar. Yield: 311 g (95.5% of theory) melting point: 153°–155° C., small colorless crystals.

$C_{16}H_{10}F_6O_2$ calculated: C, 55.18; H, 2.89; F, 32.74, O; 9.19. (348) found: C, 55.20; H, 3.00; F, 33.20; O, 9.00.

3) 2-(4-Carboxyphenyl)-2-(3-nitrophenyl)hexafluoropropane (V)

261 g of 2-(4-carboxyphenyl)-2-phenylhexafluoropropane were suspended in 500 ml of methylene chloride and, after addition of 188 ml of concentrated sulfuric acid, 75 ml of concentrated nitric acid were added dropwise at minus 5° to 0° C. The reaction mixture was subsequently stirred at this temperature for 1 hour and then poured onto 2,000 g of ice. The solid was filtered off and washed with water until the wash water had a pH of 3–4. Crude product 208 g, melting point 180°–185° C.

Working up of the filtrate: The organic phase was separated off, washed twice with water, dried over magnesium sulfate and concentrated. The tacky yellow residue was recrystallized twice from toluene, after which a further 30 g of crude product with a melting point of 180°–184° C. were obtained.

The combined amounts of crude product (238 g) were recrystallized twice from toluene, after which 186 g (63% of theory) of a white solid which had a purity, determined by gas chromatography, of 99.2% were obtained.

$^1H$ NMR (CDCl$_3$) δ (ppm): 7.5–7.7 m 4H, 8.1–8.4 m 4H, 11.1 s 1H $^{19}F$ NMR (CDCl$_3$) δ (ppm): −64.0 s IR (KBr pellet): 1170–1280 cm$^{-1}$ CF$_3$, 1350 and 1540 cm$^{-1}$ NO$_2$, 1700 cm$^{-1}$ C=O, 2500–3450 cm$^{-1}$ OH $C_{16}H_9F_6NO_4$ calculated: C, 48.87; H, 2.31; N, 3.56; E, 28.99; O, 16.28; (393.23) found: C, 49.20; H, 2.00; N, 3.40; F, 28.70; O, 16.50.

4) 2-(4-Carboxamidophenyl)-2-(3-nitrophenyl)hexafluoropropane (VI)

198 g of 2-(4-carboxy-phenyl)-2-(3-nitrophenyl)hexafluoropropane were introduced into a mixture of 700 ml of concentrated sulfuric acid and 350 ml of oleum (65% strength). After addition of 200 g of amidosulfonic acid, the reaction mixture was heated at 90°–95° C. for 3 hours. The suspension was cooled to about 20° C. and poured onto about 6 kg of ice, while stirring continuously. The solid which had precipitated was then filtered off and washed neutral with water.

Yield: 191 g (97% of theory) of white solid
Melting point: 147°–148° C.

$^1H$ NMR (CDCl$_3$) δ (ppm):. 6.6 broad s 2H, 7.4–7.9 m 6H, 8.3–8.4 m 2H $^{19}F$ NMR (CDCl$_3$) δ (ppm): −64.1 s IR (KBr pellet): 1140–1260 cm$^{-1}$ CF$_3$, 1620 and 1660 cm$^{-1}$ CONH$_2$, 3200 and 3400 cm$^{-1}$ NH$_2$ $C_{16}H_{10}F_6N_2O_3$ calculated: C, 48.98; H, 2.57; N, 7.14; (392.26) found: C, 49.40; H, 2.60; N, 7.20.

5) 4,4'-Bis[2-(3-nitrophenyl)hexafluoroisopropyl]azobenzene (VII)

157 g of 2-(4-carboxamidophenyl)-2-(3-nitrophenyl)-hexafluoropropane were introduced into a mixture of 900 ml of 13% strength aqueous sodium hypochloride solution, 150 ml of 50% strength sodium hydroxide solution and 5 ml of tricaprylylmethylammonium chloride at 0° to 5° C. The suspension was stirred for 24 hours, during which the reaction temperature should not exceed 50° C. The reaction mixture was neutralized with dilute acetic acid and the solid was filtered off and washed with water. After recrystallization of the dried crude product (149 g), 61 g of a solid of melting point 185°–187° C. were obtained. Working up of the mother liquor gave a further 14 g of the product.

Yield: 75 g (52% of theory)

$^1H$ NMR (CDCl$_3$) (ppm): 7.5–8.0 m 12H, 8.3–8.4 m 4H $^{19}F$ NMR (CDCl$_3$) (ppm): −64.1 s IR (KBr pellet): 1140–1260 cm$^{-1}$ CF$_3$, 1350 and 1540 cm$^{-1}$ NO$_2$ $C_{30}H_{16}F_{12}N_4O_4$ calculated: C, 49.73; H, 2.23; N, 7.73; (724.46) found: C, 49.60; H, 2.40; N, 7.50.

6) 2-(3-Aminophenyl)-2-(4-aminophenyl)hexafluoropropane (II)

74.2 g of 4,4'-bis[2-(3-nitrophenyl)hexafluoroisopropyl]azobenzene were dissolved in 600 ml of ethyl acetate and, after addition of 1 g of Pd/C, 5% strength, were reduced with hydrogen (100 bar) in an autoclave, initially at 25° C., and at 100° C. as the reaction subsided. After removal of the catalyst by filtration, the solvent was separated off. The residue was taken up in dilute hydrochloric acid and treated with active charcoal. The colorless filtrate obtained therefrom was neutralized with half-concentrated ammonia solution. The precipitate which separated out here was filtered off, washed with water and dried to constant weight.

Yield: 48 g (72% of theory) of white solid
Melting point: 142°–143° C.

$^1H$ NMR (CDCl$_3$) δ (ppm): 3.7 broad s 4H, 6.6–6.9 m 5H, 7.0–7.2 m 3H $^{19}F$ NMR (CDCl$_3$) δ (ppm) −64.3 s $C_{15}H_{12}F_6N_2$ calculated: C, 53.89; H, 3.62; F, 34.10; N, 8.38; (334.27) found: C, 53.50; H, 3.50; F, 33.90; N, 8.20.

7) 2-(3-Aminophenyl)-2-(4-carboxyphenyl)hexafluoropropane and

2-(3-aminophenyl)-2-(4-carboxamidophenyl)hexafluoropropane

The corresponding aminophenyl compounds were obtained from 2-(4-carboxyphenyl)-2-(3-nitrophenyl)-hexafluoropropane (V) and 2-(4-carboxamidophenyl)-2-(3-nitrophenyl)hexafluoropropane (VI) in a procedure analogous to that in Example 6.

We claim:

1. A process for the preparation of the compound of the formula (II)

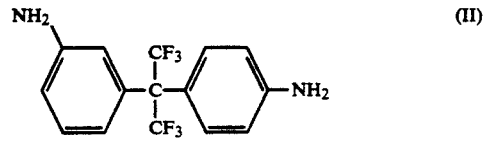

in a multi-stage process, which comprises
1a) subjecting 2-(4-methylphenyl)hexafluoropropan-2-ol to a condensation reaction with benzene in the presence of hydrogen fluoride or 1b) subjecting 2-phenylhexafluoropropan-2-ol to a condensation reaction with toluene in the presence of hydrogen fluoride.
2) oxidizing the resulting 2-(4-methylphenyl)-2-phenylhexafluoropropane (III) to give the corresponding carboxylic acid derivative (IV),
3) obtaining 2-(4-carboxyphenyl)-2-(3-nitrophenyl)-hexafluoropropane (V) from (IV) by nitration and then
4) converting this into 2-(4-carboxamidophenyl)-2-(3-nitrophenyl)hexafluoropropane (VI) by reaction with amidosulfonic acid,
5) forming 4,4'-bis[2-(3-nitrophenyl)hexafluoroisopropyl]azobenzene (VII) from (VI) by reaction with an alkali metal hypohalide solution in an alkaline medium and then
6) reducing the product to give 2-(3-aminophenyl)-2-(4-aminophenyl)hexafluoropropane (II).

2. The process as claimed in claim 1, wherein a minor amount of 2-(3-nitrophenyl)-2-(4-aminophenyl)hexafluoropropane (VIIa) is formed in stage 5) in addition to the compound (VII).

3. The process as claimed in claim 1, wherein the reduction in stage 6) is carried out catalytically with a hydrogenation catalyst of a transition metal of the Period Table or by a stoichiometric method.

4. The process as claimed in claim 3, wherein the transition metal is at least one metal of sub-group VIII.

5. The process as claimed in claim 1, wherein the compounds (V), (VI) and (VIIa) are reduced in accordance with stage 6) to give the corresponding amino compounds.

6. The process as claimed in claim 1, wherein the oxidation of the compound (III) is carried out by passing atmospheric oxygen into an acid organic medium at temperatures of 120° to 220° C. under a pressure between 5 and 40 bar in the presence of a mixture of compounds of the metals Co and Mn and of bromide ions.

7. The process as claimed in claim 6, wherein the bromide ion is employed in the form of a bromide or as a solution of hydrogen bromide in water or glacial acetic acid.

8. The process as claimed in claim 6, wherein the ratio of cobalt to manganese is 3:1 to 1:3, the sum of the concentrations of the two elements cobalt and manganese being 0.01–0.20 g atoms/kg of total reaction mass.

9. The process as claimed in claim 8, wherein the ratio of cobalt to manganese is 1:1.

10. The process as claimed in claim 8, wherein the sum of the concentrations of the two elements cobalt and manganese being 0.02–0.12 g atoms/kg of total reaction mass.

11. The process as claimed in claim 8, wherein the sum of the concentrations of the two elements cobalt and manganese being 0.04–0.08 g atoms/kg.

12. The process as claimed in claim 8, wherein the catalyst contains cerium as an additional metal ion in a ratio of the sum of cobalt and manganese to cerium of 1:0.02–2.

13. The process as claimed in claim 12, wherein the metal ions of cobalt, manganese and cerium are added in the form of acetate compounds.

14. The process as claimed in claim 12, wherein the ratio of the sum of cobalt and manganese to cerium is 1:0.05–1.

15. The process as claimed in claim 12, wherein the ratio of the sum of cobalt and manganese to cerium is 1:0.2–0.6.

* * * * *